United States Patent [19]

Berg et al.

[11] Patent Number: 5,196,094
[45] Date of Patent: * Mar. 23, 1993

[54] SEPARATION OF 1,1,1-TRICHLOROETHANE FROM THE LOWER ALCOHOLS BY EXTRACTIVE DISTILLATION

[75] Inventors: Lloyd Berg, 1314 S. Third Ave., Bozeman, Mont. 59715; Zuyin Yang, Bozeman, Mont.

[73] Assignee: Lloyd Berg, Bozeman, Mont.

[*] Notice: The portion of the term of this patent subsequent to Jun. 2, 2009 has been disclaimed.

[21] Appl. No.: 789,286

[22] Filed: Nov. 8, 1991

[51] Int. Cl.$^5$ .................. B01D 3/40; C07C 17/38; C07C 29/84
[52] U.S. Cl. .................... 203/57; 203/58; 203/60; 203/62; 203/63; 203/64; 568/913; 570/262
[58] Field of Search .................... 203/57, 58, 60, 62, 203/63, 64, 65; 570/262; 568/913, 918

[56] References Cited

U.S. PATENT DOCUMENTS

| | | | |
|---|---|---|---|
| 2,308,170 | 1/1943 | Green et al. | 570/262 |
| 3,113,079 | 12/1963 | Bergeron | 570/262 |
| 3,658,657 | 4/1972 | Bursack et al. | 570/262 |
| 3,989,601 | 11/1976 | Boozalis et al. | 570/262 |
| 4,220,609 | 9/1980 | McEntee et al. | 570/262 |
| 5,106,460 | 4/1992 | Berg | 570/262 |
| 5,118,392 | 6/1992 | Berg | 203/57 |
| 5,131,985 | 7/1992 | Berg et al. | 570/262 |

FOREIGN PATENT DOCUMENTS 142183 6/1980 German Democratic Rep. ... 203/64

Primary Examiner—Wilbur Bascomb, Jr.

[57] ABSTRACT

1,1,1-Trichloroethane cannot be completely separated from methanol, ethanol, n-propanol, isopropanol, 2-butanol or t-butanol by conventional distillation or rectification because of the minimum boiling azeotropes. 1,1,1-Trichloroethane can be readily separated from these alcohols by extractive distillation. A typical effective agent is dimethylsulfoxide.

9 Claims, No Drawings

SEPARATION OF 1,1,1-TRICHLOROETHANE FROM THE LOWER ALCOHOLS BY EXTRACTIVE DISTILLATION

FIELD OF THE INVENTION

This invention relates to a method for separating 1,1,1-trichloroethane from the lower alcohols using certain organic the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrss or more higher that the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

1,1,1-Trichloroethane, B. P. = 74° C. forms minimum boiling azeotropes with the lower alcohols. With methanol, the azeotrope boils at 61° C. and contains 20% 1,1,1-trichloroethane; with ethanol, the azeotrope boils at 63° C. and contains 75% 1,1,1-trichloroethane; with isopropanol, the azeotrope boils at 65° C. and contains 80% 1,1,1-trichloroethane; with n-propanol the azeotrope boils at 69.5° C. and contains 85% 1,1,1-trichloroethane; with 2-butanol the azeotrope boils at 70.5° C. and contains 90% 1,1,1-trichloroethane; with t-butanol the azeotrope boils at 66° C. and contains 80% 1,1,1-trichloroethane. Extractive distillation would be an attractive method of effecting the separation of 1,1,1-trichloroethane from these alcohols if agents can be found that (1) will enhance the relative volatility between 1,1,1-trichloroethane and these alcohols and (2) are easy to recover, that is, form no azeotrope 1,1,1-trichloroethane or the alcohols and boil sufficiently above 1,1,1-trichloroethane and these alcohols to make separation by rectification possible with only a few theoretical plates.

Extractive distillation typically requires the addition of an equal amount to twice as much extractive agent as the 1,1,1-trichloroethane-alcohol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Celcius degrees or more difference. It is also desirable that the extractive agent be miscible with overhead products otherwise it will form a two phase azeotrope with them and some other method of separation will have to be employed.

TABLE 1

Effect of Relative Volatility on the Separation of 1,1,1-Trichloroethane From Alcohols at 99% Purity

| Relative Volatility | Theoretical Plates | Actual Plates 75% Efficiency | Actual Plates 75% Eff., Min. Reflux |
|---|---|---|---|
| 1.2 | 50 | 67 | 87 |
| 1.5 | 23 | 31 | 40 |
| 2.0 | 13 | 17 | 22 |
| 3.0 | 9 | 12 | 16 |

The advantage of employing an effective extractive distillation agent is shown in Table 1. 1,1,1-trichloroethane forms minimum boiling azeotropes with the lower alcohols which possess a relative volatility of 1.0 and cannot be separated by rectification. If extractive distillation is employed with an agent yielding a relative volatility of 2.0, a rectification column of only 22 actual plates will be required

OBJECTIVE OF THE INVENTION

The objects of this invention are to provide a process or method of extractive distillation that will enhance the relative volatility of 1,1,1-trichloroethane to methanol, ethanol, n-propanol, isopropanol, 2-butanol and t-butanol in their separation in a rectification column. It is a further object of this invention to identify organic compounds that are stable, can be separated from 1,1,1-trichloroethane or the alcohols by rectification with relatively few plates and can be recycled to the extractive distillation column with little decomposition

SUMMARY OF THE INVENTION

The objects of this invention are provided by a process for the separation of 1,1,1-trichloroethane from methanol, ethanol, n-propanol, isopropanol, 2-butanol or t-butanol which entails the use of certain compounds as the agent in extractive distillation.

DETAILED DESCRIPTION OF THE INVENTION

I have discovered that certain organic compounds will effectively increase the relative volatility between 1,1,1-trichloroethane and methanol, ethanol, n-propanol, isopropanol, 2-butanol or t-butanol by rectification when employed as the agent in extractive distillation. Table 2 lists the compounds that I have found to be effective extractive distillation agents to recover 1,1,1-trichloroethane from methanol. The data in Tables 2, 4, 5,7,8,10, 11, 13, 15 and 16 was obtained in a vapor-liquid equilibrium still. In every case, the starting mixture was the 1,1,1,-trichloroethane - alcohol azeotrope. The relative volatilities are listed for each of the agents.

The compounds which are effective extractive distillation agents to remove 1,1,1-trichloroethane from methanol are dimethylsulfoxide, sulfolane, dimethylformamide, dimethylacetamide, acetophenone, 1-methyl-2-pyrrolidone, ethylene glycol methyl ether, ethylene glycol ethyl ether, ethylene glycol butyl ether, ethylene glycol phenyl ether, ethylene glycol hexyl ether, diethylene glycol methyl ether, diethylene glycol ethyl ether, diethylene glycol butyl ether, propylene glycol methyl ether, diethylene glycol hexyl ether, dipropylene glycol methyl ether, propylene glycol isobutyl ether, tripropylene glycol methyl ether, propoxypropanol, butoxypropanol, propylene carbonate, isophorone, diethylene glycol diethyl ether, ethylene carbonate, isoamyl alcohol, 2-ethyl butanol, 4-methyl-2-pentanol, heptyl alcohol, isooctyl alcohol, diisobutyl carbinol, isodecyl alcohol, n-decanol, 2-octanol, benzyl alcohol, tetrahydrofurfuryl alcohol, methyl isoamyl ketone, diisobutyl ketone, 2-heptanone, isobutyl heptyl ketone, 3-heptanone, propylene glycol methyl ether acetate, dipropylene glycol methyl ether acetate, propylene glycol phenyl ether, 2,4-pentanedione, methyl benzoate, methyl salicylate, adiponitrile, amyl acetate, 4-methyl pentyl acetate-2, hexyl acetate, 2-ethyl hexyl acetate, benzyl acetate, isobornyl acetate, ethylene glycol ethyl ether acetate, ethylene glycol butyl ether acetate, diethylene glycol ethyl ether acetate, 1-methoxy-2-propanol acetate, dipropylene glycol methyl ether acetate, isobutyl isobutyrate, 1-methoxy-2-acetoxy propanol, ethyl isovalerate, isobutyl butyrate, ethyl n-valerate, n-hexyl formate, ethyl acetoacetate, diethyl maleate, nitrobenzene, nitroethane, 1-nitropropane and 2-nitropropane.

TABLE 2

Effective Agents For Separating 1,1,1-Trichloroethane From Methanol

| Compounds | Relative Volatility |
|---|---|
| Dimethylsulfoxide | 2.6 |
| Sulfolane | 2.9 |
| Dimethylformamide | 2.8 |
| Dimethylacetamide | 2.5 |
| Acetophenone | 2.3 |
| 1-Methyl-2-pyrrolidinone | 2.7 |
| Ethylene glycol methyl ether | 4.0 |
| Ethylene glycol ethyl ether | 4.0 |
| Ethylene glycol butyl ether | 3.2 |
| Ethylene glycol phenyl ether | 3.1 |
| Ethylene glycol hexyl ether | 3.1 |
| Diethylene glycol methyl ether | 3.3 |
| Diethylene glycol ethyl ether | 2.9 |
| Diethylene glycol butyl ether | 2.1 |
| Propylene glycol methyl ether | 3.1 |
| Diethylene glycol hexyl ether | 4.2 |
| Dipropylene glycol methyl ether | 4.3 |
| Propylene glycol isobutyl ether | 2.5 |
| Tripropylene glycol methyl ether | 3.2 |
| Propoxypropanol | 3.0 |
| Butoxypropanol | 2.7 |
| Propylene carbonate | 2.6 |
| Isophorone | 2.4 |
| Diethylene glycol diethyl ether | 2.7 |
| Ethylene carbonate | 3.3 |
| Isoamyl alcohol | 2.2 |
| 2-Ethyl butanol | 1.4 |
| 4-Methyl-2-pentanol | 4.2 |
| Heptyl alcohol | 3.6 |
| Isooctyl alcohol | 2.5 |
| Diisobutyl carbinol | 2.4 |
| Isodecyl alcohol | 2.3 |
| n-Decanol | 2.5 |
| 2-Octanol | 2.8 |
| Benzyl alcohol | 3.0 |
| Tetrahydro furfuryl alcohol | 3.3 |
| Methyl isoamyl ketone | 2.3 |
| Diisobutyl ketone | 2.7 |
| 2-Heptanone | 3.2 |
| Isobutyl heptyl ketone | 4.4 |
| 3-Heptanone | 1.5 |
| Propylene glycol methyl ether acetate | 2.3 |
| Dipropylene glycol methyl ether acetate | 2.2 |
| Propylene glycol phenyl ether | 3.1 |
| 2,4-Pentanedione | 2.7 |
| Methyl benzoate | 2.2 |
| Methyl salicylate | 2.4 |
| Adiponitrile | 1.9 |
| Amyl acetate | 2.1 |
| 4-Methyl pentyl acetate-2 | 2.9 |
| Hexyl acetate | 1.9 |
| 2-Ethyl hexyl acetate | 2.0 |
| Benzyl acetate | 2.5 |
| Isobornyl acetate | 2.5 |
| Ethylene glycol ethyl ether acetate | 2.5 |
| Ethylene glycol butyl ether acetate | 2.1 |
| Diethylene glycol ethyl ether acetate | 2.8 |
| 1-Methoxy-2-propanol acetate | 1.7 |
| Dipropylene glycol methyl ether acetate | 3.6 |
| 1-Methoxy-2-acetoxy propanol | 2.3 |
| Isobutyl isobutyrate | 1.9 |
| Ethyl isovalerate | 2.7 |
| Isobutyl butyrate | 4.0 |
| Ethyl n-valerate | 2.7 |
| n-Hexyl formate | 1.7 |
| Ethyl acetoacetate | 2.8 |
| Diethyl maleate | 2.6 |
| Nitrobenzene | 2.5 |
| Nitroethane | 2.8 |
| 2-Nitropropane | 2.0 |
| 1-Nitropropane | 2.1 |

TABLE 3

Data From Run Made In Rectification Column

| Agent | Column | Time hrs. | Weight % CH3CCl3 | Weight % Methanol | Relative Volatility |
|---|---|---|---|---|---|
| Dimethylsulfoxide | Overhead | 1 | 90.2 | 9.8 | 2.13 |
| | Bottoms | | 3.5 | 96.5 | |
| | Overhead | 1.5 | 90.2 | 9.8 | 2.6 |
| | Bottoms | | 0.8 | 99.2 | |

One of the agents, dimethylsulfoxide, whose relative volatlity had been determined in the vapor-liquid equilibruim still, was then evaluated in a glass perforated plate column and the results listed in Table 3. Dimethylsulfoxide gave a relative volatility of 2.6 after 1.5 hours of operation.

Table 4 lists the compounds found to be effective extractive distillatio agents to recover 1,1,1-trichloroethane from ethanol. The effective agents are n-propyl acetate, isopropyl acetate, isobutyl acetate, isoamyl acetate, n-butyl acetate, n-amyl acetate, isobornyl acetate, 4-methyl-pentyl acetate-2, ethylene glycol ethyl ether acetate, ethyl phenyl acetate, benzyl acetate, ethyl acetoacetate, ethylene glycol diacetate, isobutyl butyrate, isobutyl isobutyrate, ethyl valerate, ethyl butyrate, ethyl isovalerate, methyl benzoate, ethyl benzoate, methyl salicylate, ethyl 3-ethoxy propionate, diethyl maleate, hexyl formate, isophorone, 4-methyl-2-pentanone, 2-heptanone, methyl isobutyl ketone, methyl isoamyl ketone, 2,6-dimethyl-4-heptanone, diisobutyl ketone, 2-octanone, isobutyl heptyl ketone, 2-undecanone, 3,3-dimethyl-2-butanone, 1-methyl-2-pyrrolidinone, dimethylsulfoxide, dimethylformamide, dimethylacetamide, sulfolane, acetophenone, adiponitrile, isooctyl alcohol, isobutanol, 2-butanol, 1-butanol, 1-pentanol, t-amyl alcohol, 4-methyl-2-pentanol, tetrahydrofurfuryl alcohol, diacetone alcohol, 1-methoxy-2-propanol, 3-methyl-1-butanol, ethylene carbonate, propylene carbonate, ethylene glycol methyl ether, ethylene glycol ethyl ether, ethylene glycol hexyl ether, propylene glycol methyl ether, propoxypropanol, butoxypropanol, diethylene glycol methyl ether, diethylene glycol ethyl ether, dipropylene glycol methyl ether, ethylene glycol butyl ether acetate, ethylene glycol isobutyl ether, diethylene glycol diethyl ether and anisole.

Table 5 lists the compounds that were found to be ineffective agents for separating 1,1,1-trichloroerhane from ethanol.

One of the agents, dimethylsulfoxide, whose relative volatlity had been determined in the vapor-liquid equilibrium still, was then evaluated in the glass perforated plate rectification column and the results listed in Table 6. Dimethylsulfoxide gave a relative volatility of 2.6 after 1.5 hours of operation.

TABLE 4

Effective Agents For Separating 1,1,1-Trichloroethane From Ethanol

| Compounds | Relative Volatility |
|---|---|
| Isopropyl acetate | 1.6 |
| Isobutyl acetate | 1.3 |
| Isoamyl acetate | 1.25 |
| Isobutyl butyrate | 1.25 |
| Isobutyl isobutyrate | 3.3 |
| Ethyl valerate | 1.6 |
| n-Butyl acetate | 3.5* |
| n-Amyl acetate | 1.85* |
| 4-Methyl pentyl acetate-2 | 1.45* |
| Ethylene glycol ethyl ether acetate | 1.5* |
| Isobornyl acetate | 1.6* |
| Ethyl phenyl acetate | 1.5* |
| Ethyl butyrate | 1.2* |
| Ethyl isovalerate | 1.4 |
| Benzyl acetate | 1.2 |
| n-Propyl acetate | 1.85 |
| Ethyl aceto acetate | 1.7 |
| Methyl benzoate | 1.45 |
| Ethyl benzoate | 1.55 |
| Methyl salicylate | 1.55 |
| Ethyl 3-ethoxy propionate | 1.6 |
| Diethyl maleate | 1.8 |
| Hexyl formate | 1.4 |
| Ethylene glycol diacetate | 1.7 |
| Isophorone | 1.55 |
| 4-Methyl-2-pentanone | 1.6 |
| 2-Heptanone | 1.3 |
| Methyl isobutyl ketone | 1.85 |
| Methyl isoamyl ketone | 2.0 |
| 2,6-Dimethyl-4-heptanone | 1.65 |
| Diisobutyl ketone | 1.7 |
| 2-Octanone | 1.45 |
| Isobutyl heptyl ketone | 1.4 |
| 3,3-Dimethyl-2-butanone | 1.65 |
| 2-Undecanone | 1.4 |
| 1-Methyl-2-pyrrolidinone | 2.5 |
| Dimethylsulfoxide | 2.6 |
| Dimethylformamide | 2.0 |
| Dimethylacetamide | 2.1 |
| Sulfolane | 2.2 |
| Acetophenone | 1.35 |
| Adiponitrile | 2.0 |
| Isooctyl alcohol | 2.1 |
| Isobutanol | 1.35 |
| 2-Butanol | 2.0 |
| 1-Butanol | 3.5 |
| 1-Pentanol | 3.0 |
| t-Amyl alcohol | 1.5 |
| 4-Methyl-2-pentanol | 2.1 |
| Tetrahydro furfuryl alcohol | 2.3 |
| Diacetone alcohol | 2.7 |
| 1-Methoxy-2-propanol | 2.9 |

TABLE 4-continued

Effective Agents For Separating 1,1,1-Trichloroethane From Ethanol

| Compounds | Relative Volatility |
|---|---|
| 3-Methyl-1-butanol | 2.9 |
| Ethylene carbonate | 3.2 |
| Propylene carbonate | 2.2 |
| Ethylene glycol methyl ether | 1.95 |
| Ethylene glycol ethyl ether | 2.5 |
| Ethylene glycol hexyl ether | 1.8 |
| Propylene glycol methyl ether | 2.0 |
| Propoxypropanol | 2.0 |
| Butoxypropanol | 1.95 |
| Diethylene glycol methyl ether | 3.3 |
| Diethylene glycol ethyl ether | 1.2 |
| Dipropylene glycol methyl ether | 1.85 |
| Ethylene glycol butyl ether acetate | 1.2 |
| Ethylene glycol isobutyl ether | 1.8 |
| Diethylene glycol diethyl ether | 1.2* |
| Anisole | 1.25* |

*Brings out Ethanol as Overhead

TABLE 5

Ineffective Agents, Ethanol From 1,1,1-Trichloroethane

| | |
|---|---|
| Hexyl acetate | 1-Methoxy-2-propanol acetate |
| Ethyl propionate | 3-Heptanone |
| 5-Methyl-2-hexanone | Ethylene glycol butyl ether |

TABLE 6

Data From Run Made In Rectification Column

| Agent | Column | Weight % CH$_3$CCl$_3$ | Weight % Ethanol | Time hrs. | Relative Volatility |
|---|---|---|---|---|---|
| Dimethylsulfoxide | Overhead | 97.3 | 2.7 | 1 | 2.1 |
| | Bottoms | 13.6 | 86.4 | | |
| Dimethylsulfoxide | Overhead | 99.43 | 0.57 | 1.5 | 2.6 |
| | Bottoms | 14.7 | 85.3 | | |

TABLE 7

Effective Agents From Separating 1,1,1-Trichloroethane From n-Propanol

| Compounds | Relative Volatility |
|---|---|
| Dimethylsulfoxide | 2.3 |
| Sulfolane | 3.0 |
| Dimethylformamide | 2.8 |
| Dimethylacetamide | 2.8 |
| 1-Methyl-2-pyrrolidinone | 3.0 |
| 5-Methyl-2-hexanone | 1.3 |
| 3-Heptanone | 1.25 |
| 4-Methyl-2-pentanone | 1.4 |
| Adiponitrile | 2.2 |
| 2-Octanone | 1.25 |
| 2,4-Pentanedione | 1.6 |
| 3,3-Dimethyl-2-butanone | 1.4 |
| Methyl isobutyl ketone | 1.5 |
| Isobutyl heptyl ketone | 1.25 |
| Ethylene glycol methyl ether | 4.4 |
| Ethylene glycol ethyl ether | 3.6 |
| Ethylene glycol butyl ether | 2.0 |
| Ethylene glycol hexyl ether | 1.9 |
| Ethylene glycol phenyl ether | 2.5 |
| Diethylene glycol methyl ether | 2.7 |
| Diethylene glycol butyl ether | 2.8 |
| Diethylene glycol hexyl ether | 2.0 |
| Propylene glycol methyl ether | 4.2 |
| Dipropylene glycol methyl ether | 2.5 |
| Propylene glycol isobutyl ether | 1.9 |
| Tripropylene glycol methyl ether | 2.2 |
| Propoxypropanol | 5.0 |
| Butoxypropanol | 3.0 |
| Diethylene glycol diethyl ether | 1.6 |
| Ethylene glycol diacetate | 1.7 |

TABLE 7-continued

Effective Agents From Separating 1,1,1-Trichloroethane From n-Propanol

| Compounds | Relative Volatility |
| --- | --- |
| Propylene carbonate | 2.0 |
| Isophorone | 1.8 |
| n-Butanol | 3.9 |
| Isoamyl alcohol | 3.6 |
| Isobutanol | 2.2 |
| Hexyl alcohol | 2.5 |
| Diisobutyl carbinol | 1.9 |
| Methyl benzoate | 1.25 |
| Methyl salicylate | 1.3 |
| Nitroethane | 1.9 |
| 2-Nitropropane | 1.4 |
| 1-Nitropropane | 1.3 |
| Nitrobenzene | 1.4 |
| Acetophenone | 1.7 |
| Methoxyacetoxypropane | 1.4 |
| Dipropylene glycol methyl ether acetate | 1.7 |
| Propylene glycol phenyl ether | 3.4 |
| Isobutyl butyrate | 1.3 |
| Benzyl benzoate | 1.6 |

TABLE 8

Ineffective Agents, n-Propanol From 1,1,1-Trichloroethane

| | |
| --- | --- |
| Amyl acetate | n-Butyl acetate |
| Ethyl valerate | 3-Hexanone |
| Diethylene glycol ethyl ether | Dipropylene glycol methyl ether |
| Ethyl butyrate | Ethyl isovalerate |
| n-Hexyl formate | Ethyl benzoate |

TABLE 9

Data From Run Made In Rectification Column

| Agent | Column | Time hrs. | Weight % CH₃CCl₃ | Weight % n-Propanol | Relative Volatlity |
| --- | --- | --- | --- | --- | --- |
| Dimethyl-sulfoxide | Over-head | 1 | 99.5 | 0.5 | 2.17 |
| | Bottoms | | 40 | 60 | |
| Dimethyl-sulfoxide | Over-head | 1.5 | 99.7 | 0.3 | 2.33 |
| | Bottoms | | 41.3 | 58.7 | |

Table 7 lists the compounds found to be effective extractive distillation agents to recover 1,1,1-trichloroethane from n-propanol. The effective agents are dimethylsulfoxide, sulfolane, dimethylformamide, dimethylacetamide, 1-methyl-2-pyrrolidinone, 5-methyl-2-hexanone, 3-heptanone, 4-methyl-2-pentanone, adiponitrile 2-octanone, 2,4-pentanedione, 3,3-dimethyl-2-butanone, methyl isobutyl ketone, isobutyl heptyl ketone, ethylene glycol methyl ether, ethylene glycol ethyl ether, ethylene glycol butyl ether, ethylene glycol hexyl ether, ethylene glycol phenyl ether, diethylene glycol methyl ether, diethylene glycol butyl ether, diethylene glycol hexyl ether, propylene glycol methyl ether, dipropylene glycol methyl ether, propylene glycol isobutyl ether, tripropylene glycol emthyl ether, propoxypropanol, butoxypropanol, diethylene glycol diethyyl ether, ethylene glycol diacetate, propylene carbonate, isophorone, n-butanol, isoamyl alcohol, isobutanol, hexyl alcohol, diisobutyl carbinol, methyl benzoate, methyl salicylate, nitroethane, 1-nitropropane, 2-nitropropane, nitrobenzene, acetophenone, methoxyacetoxypropane, dipropylene glycol methyl ether acetate, propylene glycol phenyl ether, isobutyl butyrate, and benzyl benzoate.

Table 8 lists the compounds that were found to be ineffective agents for separating 1,1,1,-trichloroethane from n-propanol.

One of the agents, dimethylsulfoxide, whose relative volatility had been determined in the vapor-liquid equilibrium still, was then evaluated in the glass perforated plate rectification column and the results listed in Table 9. Dimethylsulfoxide gave a relative volatility of 2.33 after 1.15 hours of operation.

The compounds which are effective extractive distillation agents to remove 1,1,1-trichloroethane from isopropanol are dimethylsulfoxide, sulfolane, dimethylformamide, dimethylacetamide, adiponitrile, amyl acetate, 2-methyl butyl acetate, hexyl acetate, 2-ethyl hexyl acetate, benzyl acetate, ethylene glycol butyl ether acetate, phenyl acetate, 1-methoxy-2-propanol acetate, isobutyl acetate, ethyl n-valerate, ethyl isovalerate, ethyl butyrate, isobutyl butyrate, isobutyl isobutyrate, methyl benzoate, methyl salicylate, butoxypropanol, 1-methyl-2-pyrrolidinone, anisole, propylene glycol methyl ether, nitroethane and propylene glycol phenyl ether and are listed in Table 10.

Table 11 lists the compounds that were found to be ineffective agents for separating 1,1,1-trichloroethane from isopropanol. One of the agents, dimethylsulfoxide, whose relative volatility had been determined in the vapor-liquid equilibrium still, was then evaluated in the glass perforated plate rectification column and the results listed in Table 12. Dimethylsulfoxide gave a relative volatility of 2.2 after 1.5 hours of operation.

The compounds which are effective extractive distillation agents to remove 1,1,1-trichloroethane from 2-butanol are dimethylsulfoxide, sulfolane, dimethylformamide, dimethylacetamide, acetophenone, 1-methyl-2-pyrrolidinone, ethylene glycol methyl ether, ethylene glycol ethyl ether, ethylene glycol butyl ether, ethylene glycol phenyl ether, ethylene glycol hexyl ether, diethylene glycol methyl ether, diethylene glycol ethyl ether, diethylene glycol butyl ether, diethylene glycol hexyl ether, propylene glycol methyl ether, dipropylene glycol methyl ether, propylene glycol isobutyl ether, tripropylene glycol methyl ether, propoxypropanol, butoxypropanol, propylene carbonate, ethylene carbonate, isophorone, diethylene glycol diethyl ether, isoamyl alcohol, 2-ethyl butanol, 4-methyl-2-pentanol, heptyl alcohol, isooctyl alcohol, diisobutyl carbinol, isodecyl alcohol, n-decanol, 2-octanol, benzyl alcohol, tetrahydrofurfuryl alcohol, methyl isoamyl ketone, diisobutyl ketone, 2-heptanone, isobutyl heptyl ketone, 3-heptanone, 2,4-pentanedione, propylene glycol methyl ether acetate, dipropylene glycol methyl ether acetate, propylene glycol phenyl ether, methyl benzoate, salicylate, adiponitrile, amyl acetate, 4-methyl pentyl acetate-2, hexyl acetate, 2-ethyl hexyl acetate, benzyl acetate, isobornyl acetate, ethylene glycol ethyl ether acetate, ethylene glycol butyl ether acetate, diethylene glycol ethyl ether acetate, 1-methoxy-2-propanol acetate, dipropylene glycol methyl ether acetate, 1-methoxy-2-acetoxy propane, isobutyl butyrate, isobutyl isobutyrate, ethyl n-valerate, ethyl isovalerate, n-hexyl formate, ethyl acetoacetate, diethyl maleate, nitrobenzene, nitroethane, 1-nitropropane and 2-nitropropane and are listed in Table 13.

TABLE 10

Effective Agents For Separating 1,1,1-Trichloroethane From Isopropanol

| Compounds | Relative Volatility |
|---|---|
| Dimethylsufoxide | 2.5 |
| Sulfolane | 1.4 |
| Dimethylformamide | 1.55 |
| Dimethylacetamide | 1.75 |
| Adiponitrile | 1.25 |
| Ethyl isovalerate | 1.6* |
| Ethyl butyrate | 1.3* |
| Isobutyl butyrate | 1.25* |
| Isobutyl acetate | 1.35* |
| 2-Methyl butyl acetate | 1.35* |
| Amyl acetate | 1.4* |
| Hexyl acetate | 1.35* |
| 2-Ethyl hexyl acetate | 1.3* |
| Benzyl acetate | 1.55* |
| Ethylene glycol butyl ether acetate | 1.3* |
| Phenyl acetate | 1.25* |
| Isobutyl isobutyrate | 1.3* |
| Methyl benzoate | 1.4 |
| Methyl salicylate | 1.45* |
| 1-Methyl-2-pyrrolidinone | 1.75 |
| Butoxypropanol | 1.3 |
| Ethyl n-valerate | 1.35* |
| Anisole | 1.55* |
| Propylene glycol methyl ether | 2.3 |
| Nitroethane | 1.3 |
| 1-Methoxy-2-propanol acetate | 1.7 |
| Propylene glycol phenyl ether | 1.6 |

*Brings Isopropanol out as Overhead

TABLE 11

Ineffecitive Agents, Isopropanol From 1,1,1-Trichlorethane

| | |
|---|---|
| n-Butyl acetate | n-Propyl acetate |
| Isopropyl acetate | Ethylene glycol ethyl ether acetate |
| Isobornyl acetate | Diethylene glycol ethyl ether acetate |
| Ethyl acetoacetate | 1-Methoxy-2-propanol acetate |
| n-Hexyl formate | Diethyl maleate |
| 3-Ethoxypropionate | Ethylene glycol diacetate |
| Nitromethane | 2-Nitropropane |
| 1-Nitropropane | Methoxyacetoxypropane |
| Isobutyl butyrate | Dipropylene glycol methyl ether acetate |
| Ethyl butyrate | |

TABLE 12

Data From Run Made In Rectification Column

| Agent | Column | Time hrs. | Weight % $CH_3CCl_3$ | Weight % Iso-propanol | Relative Volatility |
|---|---|---|---|---|---|
| Dimethyl-sulfoxide | Over-head | 1 | 99.6 | 0.4 | 2.5 |
| | Bottoms | | 27.8 | 72.2 | |
| Dimethyl-sulfoxide | Over-head | 1.5 | 98.8 | 1.2 | 2.2 |
| | Bottoms | | 23.2 | 76.8 | |

TABLE 13

Effective Agents For Separating 1,1,1-Trichloroethane From 2-Butanol

| Compounds | Relative Volatility |
|---|---|
| Dimethylsulfoxde | 2.2 |
| Sulfolane | 2.7 |
| Dimethylformamide | 2.8 |
| Dimethylacetamide | 2.5 |
| Acetophenone | 3.0 |
| 1-Methyl-2-pyrrolidinone | 3.6 |
| Ethylene glycol methyl ether | 4.5 |
| Ethylene glycol ethyl ether | 3.1 |
| Ethylene glycol butyl ether | 2.8 |
| Ethylene glycol phenyl ether | 2.0 |
| Ethylene glycol hexyl ether | 2.9 |

TABLE 13-continued

Effective Agents For Separating 1,1,1-Trichloroethane From 2-Butanol

| Compounds | Relative Volatility |
|---|---|
| Diethylene glycol methyl ether | 3.0 |
| Diethylene glycol ethyl ether | 2.8 |
| Diethylene glycol butyl ether | 2.7 |
| Diethylene glycol hexyl ether | 2.3 |
| Propylene glycol methyl ether | 3.9 |
| Dipropylene glycol methyl ether | 2.3 |
| Propylene glycol isobutyl ether | 2.4 |
| Tripropylene glycol methyl ether | 2.3 |
| Propoxypropanol | 2.7 |
| Butoxypropanol | 2.4 |
| Propylene carbonate | 2.4 |
| Isophorone | 2.0 |
| Diethylene glycol diethyl ether | 1.6 |
| Ethylene carbonate | 2.8 |
| Isoamyl alcohol | 1.6 |
| 2-Ethyl butanol | 3.3 |
| 4-Methyl-2-pentanol | 3.2 |
| Heptyl alcohol | 3.1 |
| Isooctyl alcohol | 2.4 |
| Diisobutyl carbinol | 2.2 |
| Isodecyl alcohol | 2.4 |
| n-Decanol | 2.3 |
| 2-Octanol | 2.6 |
| Benzyl alcohol | 3.5 |
| Tetrahydrofurfuryl alcohol | 3.2 |
| Methyl isoamyl ketone | 1.6 |
| Diisobutyl ketone | 1.5 |
| 2-Heptanone | 1.4 |
| Isobutyl heptyl ketone | 1.5 |
| 3-Heptanone | 1.6 |
| Propylene glycol methyl ether acetate | 1.8 |
| Dipropylene glycol methyl ether acetate | 1.8 |
| Propylene glycol phenyl ether | 2.4 |
| 2,4-Pentanedione | 1.8 |
| Methyl benzoate | 1.6 |
| Methyl salicylate | 1.3 |
| Adiponitrile | 2.7 |
| Amyl acetate | 1.5 |
| 4-Methyl pentyl acetate-2 | 1.7 |
| Hexyl acetate | 1.6 |
| 2-Ethyl hexyl acetate | 1.6 |
| Benzyl acetate | 1.7 |
| Isobornyl acetate | 1.7 |
| Ethylene glycol ethyl ether acetate | 1.9 |
| Ethylene glycol butyl ether acetate | 1.8 |
| Diethylene glycol ethyl ether acetate | 2.1 |
| 1-Methoxy-2-propanol acetate | 4.3 |
| Dipropylene glycol methyl ether acetate | 1.8 |
| 1-Methoxy-2-acetoxy propane | 2.0 |
| Isobutyl butyrate | 1.5 |
| Isobutyl isobutyrate | 1.5 |
| Ethyl n-valerate | 1.5 |
| Ethyl isovalerate | 1.6 |
| n-Hexyl formate | 1.5 |
| Ethyl aceoacetate | 1.8 |
| Diethyl maleate | 1.9 |
| Nitrobenzene | 1.6 |
| Nitroethane | 2.0 |
| 2-Nitropropane | 1.6 |
| 1-Nitropropane | 1.6 |

TABLE 14

Data From Run Made In Rectification Column

| Agent | Column | Time hrs | Weight % $CH_3Cl_3$ | Weight % 2-Butanol | Relative Volatility |
|---|---|---|---|---|---|
| Dimethyl-sulfoxide | Over-head | 1 | 99.6 | 0.4 | 2.1 |
| | Bottoms | | 53.1 | 46.9 | |
| Dimethyl-sulfoxide | Over-head | 1.5 | 99.7 | 0.3 | 2.15 |
| | Bottoms | | 55.1 | 44.9 | |

TABLE 15

Effective Agents For Separating 1,1,1-Trichloroethane From t-Butanol

| Compounds | Relative Volatility |
|---|---|
| Dimethylsulfoxide | 1.7 |
| Sulfolane | 1.4 |
| Dimethylformamide | 1.9 |
| Dimethylacetamide | 1.9 |
| Adiponitrile | 1.4 |
| Ethylene glycol methyl ether | 3.1 |
| Ethylene glycol ethyl ether | 2.2 |
| Ethylene glycol butyl ether | 1.7 |
| Ethyene glycol phenyl ether | 1.3 |
| Diethylene glycol methyl ether | 2.2 |
| Diethylene glycol ethyl ether | 1.4 |
| Diethylene glycol butyl ether | 1.5 |
| Diethylene glycol hexyl ether | 1.5 |
| Propylene glycol methyl ether | 1.7 |
| Dipropylene glycol methyl ether | 1.5 |
| Propylene glycol isobutyl ether | 1.4 |
| Tripropylene glycol methyl ether | 1.4 |
| Propoxypropanol | 3.3 |
| Butoxypropanol | 1.4 |
| Ethylene glycol diacetate | 1.3 |
| Propylene carbonate | 1.5 |
| Isophorone | 1.4 |
| n-Butanol | 2.7 |
| Isoamyl alcohol | 3.0 |
| Isobutanol | 1.2 |
| Ethylene carbonate | 1.3 |
| Hexyl alcohol | 1.2* |
| Methyl salicylate | 1.3* |

*Brings out t-Butanol as Overhead

TABLE 16

Ineffective Agents, t-Butanol From 1,1,1-Trichloroethane

| | |
|---|---|
| Amyl acetate | n-Butyl acetate |
| Ethyl valerate | 5-Methyl-2-hexanone |
| 3-Heptanone | 4-Methyl-2-pentanone |
| 2-Octanone | 2,4-Pentanedione |
| Methyl isobutyl ketone | 3,3-Dimethyl2-butanone |
| Isobutyl heptyl ketone | 3-Ethoxypropionate |
| Anisole | Diethylene glycol diethyl ether |
| Methyl benzoate | |

One of the agents, dimethylsulfoxide, whose relative volatility had been determined in the vapor-liquid equilibrium still, was then evaluated in the glass perforated plate rectification column and the results listed in Table 14. Dimethylsulfoxide gave a relative volatility of 2.15 after 1.5 hours of operation.

The compounds which are effective extractive distillation agents to remove 1,1,1-trichloroethane from t-butanol are listed in Table 15 and are dimethylsulfoxide, dimethylformamide, dimethylacetamide, adiponitrile, ethylene glycol methyl ether, ethylene glycol ethyl ether, ethylene glycol butyl ether, ethylene glycol phenyl ether, diethylene glycol methyl ether, diethylene glycol ethyl ether, diethylene glycol butyl ether, diethylene glycol hexyl ether, propylene glycol methyl ether, dipropylene glycol methyl ether, propylene glycol isobutyl ether, tripropylene glycol methyl ether, propoxypropanol, butoxypropanol, ethylene glycol diacetate, propylene carbonate, isophorone, n-butanol, isoamyl alcohol, isobutanol, ethylene carbonate, alcohol and methyl salicylate.

Table 16 lists the compounds that were found to be ineffective agents for separating 1,1,1-trichloroethane from t-butanol.

One of the agents, dimethylsulfoxide, whose relative volatility had been determined in the vapor-liquid equilibrium still, was then evaluated in the glass perforated rectification column and the results listed in Table 17. Dimethylsulfoxide gave a relative volatility of 1.68 after 1.5 hours of operation.

TABLE 17

Data From Run Made In Rectification Column

| Agent | Column | Weight % CH$_3$CCl$_3$ | Weight % t-Butanol | Time hrs. | Relative Volatility |
|---|---|---|---|---|---|
| Dimethylsulfoxide | Overhead | 97.1 | 2.9 | 1 | 1.68 |
| | Bottoms | 43.4 | 56.6 | | |
| Dimethylsulfoxide | Overhead | 95.7 | 4.3 | 1.5 | 1.68 |
| | Bottoms | 33.5 | 66.5 | | |

THE USEFULNESS OF THE INVENTION

The usefulness or utility of this invention can be demonstrated by referring to the data presented in Tables 2 to 17. All of the successful agents show that 1,1,1-trichloroethane can be separated from methanol, ethanol, n-propanol, isopropanol, 2-butanol and t-butanol by means of extractive distillation in a rectification column and that the ease of separation as measured by relative volatility is considerable.

WORKING EXAMPLES

Example 1

Seventy grams of the 1,1,1-trichloroethane-methanol azeotrope and 30 grams of dimethylsulfoxide were charged to a vapor-liquid equilibrium still and refluxed for eight hours. Analysis indicated a vapor composition of 24.2% 1,1,1-trichloroethane, 75.8% methanol; a liquid composition of 11% 1,1,1-trichloroethane, 89% methanol which is a relative volatility of 2.6.

Example 2

A solution comprising 250 grams of the 1,1,1-trichloroethane-methanol azeotrope was placed in the stillpot of a 7.3 theoretical plate glass perforated plate rectification column. When refluxing began, an extractive agent comprising dimethylsulfoxide was pumped into the column at a rate of 15 ml/min. The temperature of the extractive agent as it entered the top of the column was 65° C. After establishing the feed rate of the extractive agent, the heat input to the 1,1,1-trichloroethane-methanol in the stillpot was adjusted to give a total reflux rate of 40 ml/min. After 1.5 hours operation, overhead and bottoms samples were collected and analysed by gas chromatography. The overhead analysis was 90.2% 1,1,1-trichloroethane, 9.8% methanol and the bottoms analysis was 0.8% 1,1,1-trichloroethane, 99.2% methanol. This gives an average relative volatility of 2.6 for each theoretical plate. This data is in Table 3.

Example 3

A solution comprising 250 grams of the 1,1,1-trichloroethane ethanol azeotrope was placed in the stillpot of the 7.3 theoretical plate rectification column. When refluxing began, an extractive agent comprising dimethylsulfoxide was pumped into the column at a rate of 15 ml/min. The temperature of the extractive agent as it entered the top of the column was 70° C. After establishing the feed rate of the extractive agent, the heat input to the 1,1,1-trichloroethane ethanol in the stillpot was adjusted to give a total reflux rate of 40 ml/min. After 1.5 hours operation, overhead and bottoms samples were collected and analysed. The overhead analysis was 99.43% 1,1,1-trichloroethane, 0.57% ethanol and the bottoms analysis was 14.7% 1,1,1-trichloroethane, 85.3% ethanol. This gives an average relative volatility of 2.6 for each theoretical plate. This data is presented in Table 6.

Example 4

A solution comprising 250 grams of the 1,1,1-trichloroethane-n-propanol azeotrope was placed in the stillpot of the 7.3 theoretical plate rectification column. When refluxing began, an extractive agent comprising dimethylsulfoxide was pumped into the column at a rate of 15 ml/min. The temperature of the extractive agent as it entered the top of the column was 75° C. After establishing the feed rate of the extractive agent, the heat input to the 1,1,1-trichloroethane -n-propane in the stillpot was adjusted to give a total reflux rate of 40 ml/min. After 1.5 hours operation, overhead and bottoms samples were collected and analysed. The overhead analysis was 99.7% 1,1,1-trichloroethane, 0.3% n-propanol and the bottoms analysis was 41.3% 1,1,1-trichloroethane, 58.7% n-propanol. This gives an average relative volatility of 2.33 for each theoretical plate. This data is presented in Table 9.

Example 5

A solution comprising 250 grams of the 1,1,1-trichloroethane-isopropanol azeotrope was placed in the stillpot of the 7.3 theoretical plate rectification column. When refluxing began, an extractive agent comprising dimethylsulfoxide was pumped into the column at a rate of 15 ml/min. The temperature of the extractive agent as it entered the top of the column was 73° C. After establishing the feed rate of the extractive agent, the heat input to the 1,1,1-trichloroethane-isopropanol in the stillpot was adjusted to give a total reflux rate of 40 ml/min. After 1.5 hours operation, overhead and bottoms samples were collected and analysed. The overhead analysis was 98.8% 1,1,1-trichloroethanel 2% isopropanol and the bottoms analysis was23.3% 1,1,1-trichloroethane,76.8% isopropanol. This gives an average relative volatility of 2.2 for each theoretical plate. This data is presented in Table 12.

Example 6

A solution comprising 250 grams of the 1,1,1-trichloroethane-2-butanol azeotrope was placed in the stillpot of the 7.3 theoretical plate rectification column. When refluxing began, an extractive agent comprising dimethylsulfoxide was pumped into the column at a rate of 15 ml/min. The temperature of the extractive agent as it entered the column was 83° C. After establishing the feed rate of the extractive agent, the heat input to the 1,1,1-trichloroethane-2-butanol in the stillpot as adjusted to give a total reflux rate of 40 ml/min. After 1.5 hours operation, overhead and bottoms samples were collcted and analysed. The overhead analysis was 99.7% 1,1,1-trichloroetahne, 0.3% 2-butanol and the bottoms analysis was 55.1% 1,1,1-trichloroethane, 44.9% 2-butanol. This gives an average relative volatility of 2.15 for each theoretical plate. This data is presented in Table 14.

Example 7

A solution comprising 250 grams of the 1,1,1-trichloroethane-t-butanol azeotrope was placed in the stillpot of the 7.3 theoretical plate rectification column. When refluxing began, an extractive agent comprising dimethylsulfoxide was pumped into the column at a rate of 15 ml/min. The temperature of the extractive agent as it entered the top of the column was 80° C. After establishing the feed rate of the extractive agent, the heat input to the 1,1,1-trichloroethane-t-butanol in the stillpot was adjusted to give a total reflux rate of 40 ml/min. After 1.5 hours operation, overhead and bottoms samples were collected and analysed. The overhead analysis was 95.7% 1,1,1-trichloroethane, 4.3% t-butanol and the bottoms analysis was 33.5% 1,1,1-trichloroethane, 66.5% t-butanol. This gives an average relative volatility of 1.68 for each theoretical plate. This data is presented in Table 17.

We claim:

1. A method for recovering 1,1,1-trichloroethane from a mixture of 1,1,1-trichloroethane and methanol which comprises distilling a mixture of 1,1,1-trichloroethane and methanol in the presence of about one part of an extractive agent per part of 1,1,1-trichloroethane-methanol mixture, recovering the 1,1,1-trichloroethane as overhead product and obtaining the methanol and the extractive agent from the stillpot, wherein said extractive agent consists of one material selected from the group consisting of dimethylsulfoxide, sulfolane, dimethylformamide, acetophenone, dimethylacetamide,1-methyl-2-pyrrolidone, ethylene glycol methyl ether, ethylene glycol ethyl ether, ethylene glycol butyl ether, ethylene glycol phenyl ether, ethylene glycol hexyl ether, diethylene glycol methyl ether, diethylene glycol ethyl ether, diethylene glycol butyl ether, propylene glycol methyl ether, diethylene glycol hexyl ether, dipropylene glycol methyl ether, propylene glycol isobutyl ether, tripropylene glycol methyl ether, propoxypropanol, butoxypropanol, propylene carbonate, isophorone, diethylene glycol diethyl ether, ethylene carbonate, isoamyl alcohol, 2-ethyl butanol, 4-methyl-2pentanol, heptyl alcohol, isooctyl alcohol, di-butyl carbinol, isodecyl alcohol, n decanol, 2-octanol, benzyl alcohol, tetrahydrofurfuryl alcohol, methyl isoamyl ketone, diisobutyl ketone, 2-heptanone, isobutyl heptyl ketone, 3-heptanone, propylene glycol methyl ether acetate, dipropylene glycol methyl ether-acetate, propylene glycol phenyl ether, 2,4-pentanedione, methyl benzoate, methyl salicylate, adiponitrile, amyl acetate, 4-methyl pentyl acetate-2, hexyl acetate, 2-ethyl hexyl acetate, benzyl acetate, isobornyl acetate, ethylene glycol ethyl ether acetate, ethylene glycol butyl ether acetate, diethylene glycol ethyl ether acetate, 1-methoxy-2-propanol acetate, dipropylene glycol methyl ether acetate, isobutyl isobutyrate, 1-methoxy-2-acetoxy propanol, ethyl isovalerate, isobutyl butyrate, ethyl n-valerate, n-hexyl formate, ethyl acetoacetate, diethyl maleate, nitrobenzene, nitroethane, 1-nitropropane and 2-nitropropane.

2. A method for recoveringing 1,1,1-trichloroethane from a mixture of 1,1,1-trichloroethane and ethanol which comprises distilling a mixture of 1,1,1-trichloroethane and ethanol in the presence of about one part of an extractive agent per part of 1,1,1-trichloroethane-ethanol mixture, recovering the 1,1,1-trichloroethane as overhead product and obtaining the ethanol and the extractive agent from the stillpot, wherein said extractive agent consists of one material selected from the group consisting of isopropyl acetate, isobutyl acetate, isoamyl acetate, isobutyl butyrate, isobutyl isobutyrate, ethyl valerate, ethyl isovalerate, benzyl acetate, n-propyl acetate, ethyl acetoacetate, methyl benzoate, ethyl benzoate, methyl salicylate, ethyl 3-ethoxypropionate, diethyl maleate, hexyl formate, ethylene glycol diacetate, isophorone, 4-methyl-2-pentanone, 2-heptanone, methyl isobutyl ketone, methyl isoamyl ketone, 2,6-dimethyl-4-heptanone, diisobutyl ketone, 2-octanone, isobutyl heptyl ketone, 3,3-dimethyl-2-butanone, 2-undecanone, 1-methyl-2-pyrrolidinone, dimethylsulfoxide, dimethylformamide, dimethylacetamide, sulfolane, acetophenone, adiponitrile, isooctyl alcohol, isobutanol, 2-butanol, 1-butanol, 1-pentanol, t-amyl alcohol, 4-methyl-2-pentanol, tetrahydro furfuryl alcohol, diacetone alcohol, 1-methoxy-2-propanol, 3-methyl-1-butanol, ethylene carbonate, propylene carbonate, ethylene glycol methyl ether, ethylene ethyl ether, ethylene glycol hexyl ether, propylene glycol methyl ether, propoxypropanol, butoxypropanol, diethylene glycol methyl ether, diethylene glycol ethyl ether, dipropylene glycol methyl ether, ethylene glycol butyl ether acetate and ethylene glycol isobutyl ether.

3. A method for recovering 1,1,1-trichloroethane from a mixture of 1,1,1-trichloroethane and ethanol which comprises distilling a mixture of and ethanol in the presence of about one part of per part of 1,1,1-trichloroethane - ethanol mixture the ethanol as overhead product and obtaining the 1, , and the extractive agent from the stillpot, wherein said extractive agent consists of one material selected from the group consisting of n-butyl acetate, n-amyl acetate, isobornyl acetate, 4-methyl pentyl acetate-2, ethylene glycol ethyl ether acetate, ethyl phenyl acetate, ethyl butyrate, diethylene glycol diethyl ether and anisole.

4. A method for recovering 1,1,1-trichloroethane from a mixture of 1,1,1-trichloroethane and n-propanol which comprises distilling a mixture of 1,1,1-trichloroethane and n-propanol in the presence of about one part of an extractive agent per part of 1,1,1-trichloroethane-n-propanol mixture, recovering the 1,1,1-trichloroethane as overhead product and obtaining the n-propanol and the extractive agent from the stillpot, wherein said extractive agent consists of one material selected from the group consisting of dimethylsulfoxide, sulfolane, dimethylformamide, dimethylacetamide, 1-methyl-2-pyrrolidinone, 5-methyl-2-hexanone, 3-heptanone, 4-methyl 2-pentanone, adiponitrile, 2-octanone, 2,4-pentanedione, 3,3-dimethyl-2-butanone, methyl isobutyl ketone, isobutyl heptyl ketone, ethylene glycol methyl ether, ethylene glycol ethyl ether, ethylene glycol butyl ether, ethylene glycol hexyl ether, ethylene glycol phenyl ether, diethylene glycol methyl ether, diethylene glycol butyl ether, diethylene glycol hexyl ether, propylene glycol methyl ether, dipropylene glycol methyl ether, propylene glycol isobutyl ether, tripropylene glycol methyl ether, propoxypropanol, butoxypropanol, diethylene glycol diethyl ether, ethylene glycol diacetate, propylene carbonate, isophorone, n-butanol, isoamyl alcohol, isobutanol, hexyl alcohol, diisobutyl carbinol, methyl benzoate, methyl salicylate, nitroethane, 1-nitropropane, 2-nitropropane, nitrobenzene, acetophenone, methoxyacetoxypropane, dipropylene glycol methyl ether acetate, propylene glycol phenyl ether, isobutyl butyrate, and benzyl benzoate.

5. A method for recovering 1,1,1-trichloroethane from a mixture of 1,1,1-trichloroethane and isopropanol which comprises distilling a mixture of 1,1,1-trichloroethane and isopropanol in the presence of about one one part of an extractive agent per part of 1,1,1-trichloroethane-isopropanol mixture, recovering the 1,1,1-trichloroethane as overhead product and obtaining the isopropanol and the extractive agent from the stillpot, wherein said extractive agent consists of one one material selected from the group consisting of dimethlsulfoxide, sulfolane, dimethylformamide, dimethylacetamide, adiponitrile, methyl benzoate, 1-methyl-2-pyrrolidinone, butoxypropanol, propylene glycol methyl ether, nitroethane, 1-methoxy-2-propanol acetate and propylene glycol phenyl ether.

6. A method for recovering 1,1,1-trichloroethane from a mixture of 1,1,1-trichloroethane and isopropanol which comprises distilling a mixture of 1,1,1-trichloroethane and isopropanol in the presence of about one part of an extractive agent per part of 1,1,1-trichloroethane-isopropanol mixture, recovering the isopropanol as overhead product and obtaining the 1,1,1-trichloroethane and the extractive agent from the stillpot, wherein said extractive agent consists of one material selected from the group consisting of dimethlsulfoxide, ethyl butyrate, isobutyl butyrate, isobutyl acetate, amyl acetate, 2-methyl butyl acetate, hexyl acetate, 2-ethyl hexyl acetate, benzyl acetate, ethylene glycol butyl ether acetate, phenyl acetate, isobutyl isobutyrate, ethyl valerate, methyl salicylate and anisole.

7. A method for recovering 1,1,1-trichloroethane from a mixture of 1,1,1-trichloroethane and 2-butanol which comprises distilling a mixture of 1,1,1-trichloroethane and 2-butanol in the presence of about one part of an extractive agent per part of 1,1,1-trichloroethane-2-butanol mixture, recovering the 1,1,1-trichloroethane as overhead product and obtaining the 2-butanol and the extractive agent from the stillpot, wherein said extractive agent consists of one material selected from the group consisting of dimethylsulfoxide, sulfolane, dimethylformamide, dimethylacetamide, acetophenone, 1-methyl-2-pyrrolidinone, ethylene glycol methyl ether, ethylene glycol ethyl ether, ethylene glycol butyl ether, ethylene glycol phenyl ether, ethylene glycol hexyl ether, diethylene glycol methyl ether, diethylene glycol ethyl ether, diethylene glycol butyl ether, diethylene glycol hexyl ether, propylene glycol methyl ether, dipropylene glycol methyl ether, propylene glycol isobutyl ether, tripropylene glycol methyl ether, propoxypropanol, butoxypropanol, propylene carbonate, ethylene carbonate, isophorone, diethylene glycol diethyl ether, isodecyl alcohol, n-decanol, methyl isoamyl ketone, diisobutyl ketone, 2-heptanone, isobutyl heptyl ketone, 3-heptanone, 2,4-pentanedione, propylene glycol methyl ether acetate, dipropylene glycol methyl ether acetate, propylene glycol phenyl ether, methyl benzoate-ethyl salicylate, adiponitrile, amyl acetate, 4-methyl pentyl acetate-2, hexyl acetate, 2-ethyl hexyl acetate, benzyl acetate, isobornyl acetate, ethylene glycol ethyl ether acetate, ethylene glycol butyl ether acetate, diethylene glycol ethyl ether acetate, 1-methoxy-2-propanol acetate, dipropylene glycol methyl ether acetate, 1-methoxy-2-acetoxy propane, isobutyl butyrate, isobutyl isobutyrate, ethyl n-valerate, ethyl isovalerate, n-hexyl formate, ethyl acetoacetate, diethyl maleate, nitrobenzene, nitroethane, 1-nitropropane and 2-nitropropane.

8. A method for recovering 1,1,1-trichloroethane from a mixture of 1,1,1-trichloroethane and t-butanol which comprises distilling a mixture of 1,1,1-trichloroethane and t-butanol in the presence of about one part of an extractive agent per part of 1,1,1-trichloroethane-t-butanol mixture, recovering the 1,1,1-trichloroethane as overhead product and obtaining the t-butanol and the extractive agent from the stillpot, wherein said extractive agent consists of one material selected from the group consisting of dimethylsulfoxide, dimethylformamide, dimethylacetamide, adiponitrile, ethylene glycol methyl ether, ethylene glycol ethyl ether, ethylene glycol butyl ether, ethylene glycol phenyl ether, diethylene glycol methyl ether, diethylene glycol ethyl ether, diethylene glycol butyl ether, diethylene glycol hexyl ether, propylene glycol methyl ether, dipropylene glycol methyl ether, propylene glycol isobutyl ether, tripropylene glycol methyl ether, propoxypropanol, butoxypropanol, ethylene glycol diacetate, propylene carbonate, isophorone, n-butanol, isoamyl alcohol, isobutanol and ethylene carbonate.

9. A method for recovering 1,1,1-trichloroethane from a mixture of 1,1,1-trichloroethane and t-butanol which comprises distilling a mixture of 1,1,1-trichloroethane and t-butanol in the presence of about one part of an extractive agent per part of 1,1,1-trichloroethane-t-butanol mixture, recovering the t-butanol as overhead product and obtaining the 1,1,1-trichloroethane and the extractive agent from the stillpot, wherein said extractive agent consists of hexyl alcohol or methyl salicylate.

* * * * *